United States Patent
Jones

(10) Patent No.: US 9,140,672 B2
(45) Date of Patent: Sep. 22, 2015

(54) CALIBRATION BLOCK AND METHOD

(71) Applicant: AIRBUS OPERATIONS LIMITED, Bristol (GB)

(72) Inventor: Terence Jones, Chepstow (GB)

(73) Assignee: AIRBUS OPERATIONS LIMITED, Bristol (GB)

( * ) Notice: Subject to any disclaimer, the term of this patent is extended or adjusted under 35 U.S.C. 154(b) by 335 days.

(21) Appl. No.: 13/736,304

(22) Filed: Jan. 8, 2013

(65) Prior Publication Data

US 2013/0180312 A1 Jul. 18, 2013

(30) Foreign Application Priority Data

Jan. 13, 2012 (GB) .................................... 1200531.0

(51) Int. Cl.
*G01N 29/30* (2006.01)
*G01N 29/26* (2006.01)

(52) U.S. Cl.
CPC .............. *G01N 29/30* (2013.01); *G01N 29/262* (2013.01)

(58) Field of Classification Search
CPC ......... G01B 17/00; G01H 3/005; G01N 29/30
See application file for complete search history.

(56) References Cited

U.S. PATENT DOCUMENTS

| | | | | |
|---|---|---|---|---|
| 3,733,889 A * | 5/1973 | Proctor, Jr. | ...................... | 73/629 |
| 3,933,026 A * | 1/1976 | Ham et al. | ...................... | 73/1.86 |
| 4,173,139 A * | 11/1979 | Conn | ............................... | 73/1.84 |
| 4,453,408 A * | 6/1984 | Clayman | .......................... | 73/1.86 |
| 4,704,892 A * | 11/1987 | Tarnai | ................................ | 73/1.86 |
| 5,163,027 A * | 11/1992 | Miller et al. | ...................... | 367/13 |
| 5,665,893 A * | 9/1997 | Smith | ............................. | 73/1.82 |
| 5,837,880 A * | 11/1998 | Shakinovsky et al. | .......... | 73/1.86 |
| 6,415,644 B1 * | 7/2002 | Rockwood et al. | ............. | 73/1.86 |
| 7,320,241 B2 * | 1/2008 | Kollgaard et al. | .............. | 73/1.86 |
| 7,578,166 B2 * | 8/2009 | Ethridge et al. | ................ | 73/1.82 |
| 7,617,715 B2 * | 11/2009 | Georgeson et al. | ............. | 73/1.86 |
| 2004/0020296 A1 | 2/2004 | Moles et al. | | |
| 2005/0076703 A1 * | 4/2005 | Johnson et al. | ................. | 73/1.82 |
| 2005/0092091 A1 * | 5/2005 | Greelish | ........................... | 73/617 |
| 2009/0178465 A1 | 7/2009 | Ethridge et al. | | |
| 2011/0296923 A1 | 12/2011 | Cataldo et al. | | |

FOREIGN PATENT DOCUMENTS

EP   1522848 A1   4/2005

OTHER PUBLICATIONS

"Tubular, PVC-based project coming", Parts Express User Forum, available at <http://techtalk.parts-express.com/showthread.php?213242-Tubular-PVC-based-project-coming-!&s=74702a7c80310df4199caa94c4ac60dc&p=1593905#post1593905>, Sep. 21, 2009.*
Search Report corresponding to GB 1200531.0, dated Apr. 19, 2012.

* cited by examiner

*Primary Examiner* — David A Rogers
(74) *Attorney, Agent, or Firm* — Lowe Hauptman & Ham, LLP

(57) ABSTRACT

A calibration block and method for sensitivity calibration. The calibration block has a curved calibration surface having a central axis and a surface for coupling to a transducer element of an angular scanning phased array ultrasonic testing scanner. The block is configured such that the surface positions the transducer such that its scanning axis is coaxial with the central axis of the curved calibration surface.

12 Claims, 3 Drawing Sheets

CALIBRATION BLOCK AND METHOD

RELATED APPLICATIONS

The present application is based on, and claims priority from, British Application Number 1200531.0, filed Jan. 13, 2012, the disclosure of which is hereby incorporated by reference herein in its entirety.

FIELD OF THE INVENTION

The present application is concerned with a calibration block and a calibration method. More specifically, the present invention is concerned with a signal sensitivity calibration block for a phased array ultrasonic testing scanner and a method of calibrating the signal sensitivity of a phased array ultrasonic testing scanner.

BACKGROUND OF THE INVENTION

Non-visible areas of materials, such as the interiors of components, welds and composite materials can be analysed using ultrasonic testing. This type of non-destructive testing utilises the reflection of sound waves to detect faults and features which would otherwise be very difficult to detect without destroying the component in the process. Ultrasonic testing is a common technique in the aerospace sector to test the integrity of materials at manufacture and during service.

Phased array ultrasonic testing scanners generally include a transducer having a plurality of transducer elements. The array of transducer elements may be selectively energised to launch a number of individual wave fronts into a test material. The wave fronts constructively and destructively combine within the material, resulting in a primary wave front which travels through the material and reflects off cracks, discontinuities or the like therein. Such cracks, discontinuities and the like will be herein referred to as "target features". The primary wave front can be considered to define a beam. The beam can be dynamically steered across a scanning envelope by firing groups of transducer elements in a particular sequence. The sequence and related parameters (e.g. voltage) are sometimes referred to as a "focal law".

The signal response from primary wave front at a plurality of contiguous beam angles can be combined by the scanner to create a two dimensional "S-Scan" image corresponding to the scanning envelope. This type of scanner is known in the art as "sectorial" or "angular" scanning. The transducer of such a scanner has a central transmission axis and the amount by which the envelope extends from the central axis may be represented in degrees e.g. +50°>−50°, or +70°>+50°, although the envelope may also be expressed with reference to a plane, such as a central plane, or an axis of the test object. When the scanning envelope extends in both the positive and negative directions it is known as a "lateral" scan.

While it may be advantageous to increase the size of the scanning envelope, doing so can be problematic because the magnitude of a primary wave front created by the energised transducer elements may vary across the envelope. Thus, the response signal strength from a target feature at one angle from the central axis may differ to that from an identical target feature at another angle from the central axis. This may result in a loss of signal amplitude from a range of values when visualising signal response, which may relay to a user of the scanner that a target feature at, say, +50° is smaller than a target feature at, say, +20°, when in fact both target features are of the same size and equidistant from the transducer.

Some ultrasonic testing scanners can compensate for the above-mentioned problem by providing sensitivity calibration functionality. One example is the Omniscan MX scanner marketed by Olympus. The sensitivity calibration process generally involves moving the transducer along a "calibration standard" block which is provided with a cross drilled hole and using the signal response from the cross drilled hole to calibrate the control signals to the transducer elements. However, even following such sensitivity calibration, the signal response across a wide scanning envelope may be more irregular than is desirable. Following this, a separate "reference standard" block is scanned using the transducer to set the calibration gain of the ultrasonic testing scanner such that the gain is at an appropriate level to search for a target feature.

SUMMARY OF THE INVENTION

A first aspect of the invention provides a calibration block for calibrating the signal sensitivity of an angular scanning phased array ultrasonic testing scanner. The angular scanning phased array ultrasonic testing scanner is arranged to generate a primary wave front at a plurality of contiguous beam angles across a scanning envelope. The calibration block may be formed of an acoustically transmissive material. The calibration block may comprise first major surface having a peripheral edge. The calibration block may comprise a second major surface. The calibration block may comprise a calibration surface disposed between general planes of the first and second major surfaces. The calibration surface may be configured to extend in a generally circular arc so as to be generally equidistant from a central axis. The peripheral edge of the first surface may be spaced further from the central axis than the calibration surface. The calibration block may comprise an input surface for acoustically coupling to an ultrasound transducer of the ultrasonic testing scanner. The calibration block may be arranged to position the transducer such that the path length of the primary wave front from the transducer to the calibration surface is generally equal for each beam angle across the scanning envelope.

Thus, the calibration block may be used to calibrate the signal sensitivity of an angular scanning phased array ultrasonic testing scanner having a signal sensitivity calibration program. Calibration may be performed across a scanning envelope which is less than or equal to the angular extension of the calibration surface. The calibration surface may be considered to define an acoustically reflective "shoulder", which can be sized to enable the calibration block to be used as a calibration standard for signal sensitivity normalisation and additionally for setting an appropriate gain level, thereby simplifying the calibration process.

The input surface may be generally parallel with respect to the central axis of the calibration surface.

The input surface may be parallel with respect to a tangential plane to the calibration surface.

The size of the calibration surface may be selected to be representative of a defect the scanner is arranged to detect.

The calibration surface may have a semicircular profile. This advantageously enables a calibration block according to embodiments of the present invention to be used to calibrate signal sensitivity across a scanning envelope which is greater than +50°>−50° and in some cases may be close to +90°>−90°. The peripheral edge of the first surface may be spaced further from the central axis than the calibration surface by at least ¼ of the distance between the central axis and the calibration surface.

A second aspect of the invention provides the use of a calibration block according to the first aspect for calibrating the signal sensitivity and gain of a phased array testing scanner.

A third aspect of the invention provides a method for calibrating the signal sensitivity of an angular scanning phased array ultrasonic testing scanner, the method comprising: providing a calibration block according to the first aspect; coupling an ultrasound transducer of the ultrasonic testing scanner to the input surface of the calibration block; and operating the sensitivity calibration program of the ultrasonic testing scanner to calibrate the signal sensitivity of the ultrasonic testing scanner by measuring the signal response from the calibration surface.

The method may include the step of calibrating the signal gain of the ultrasonic testing scanner by measuring the signal response from the calibration surface.

The scanning envelope may be at least 90° and preferably at least 110°. In other embodiments the range may be any combination of negative and/or positive angles which lie within the physical boundary of the block.

The ultrasonic testing scanner may be an Omniscan MX scanner or other angular scanning phased array ultrasonic testing scanner having a signal sensitivity calibration program.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
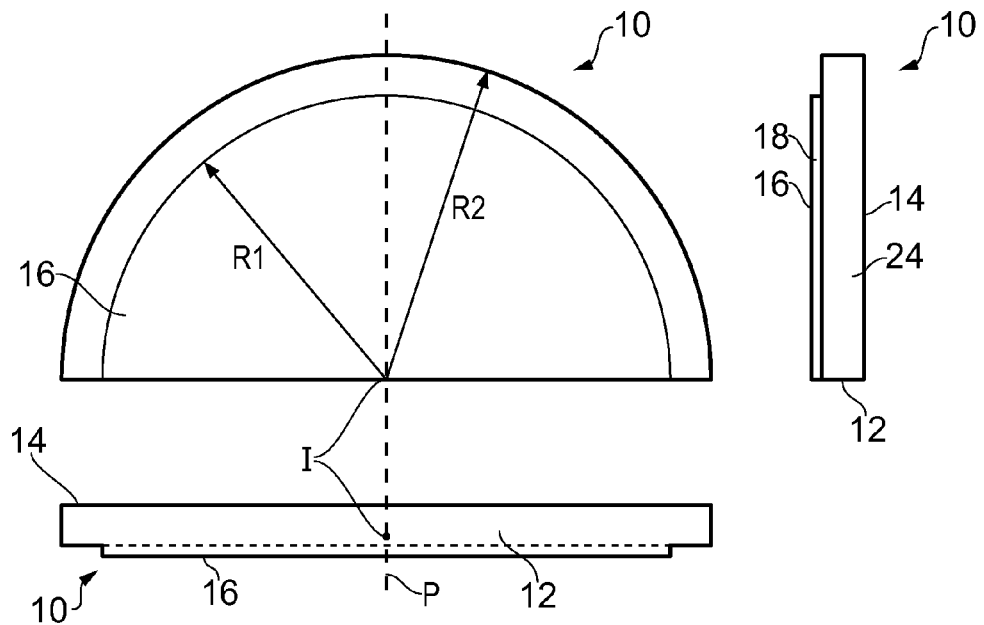
FIG. 1 is an orthographic projection showing front, side and base views of a calibration block according to an embodiment of the present invention.
Figure 2:
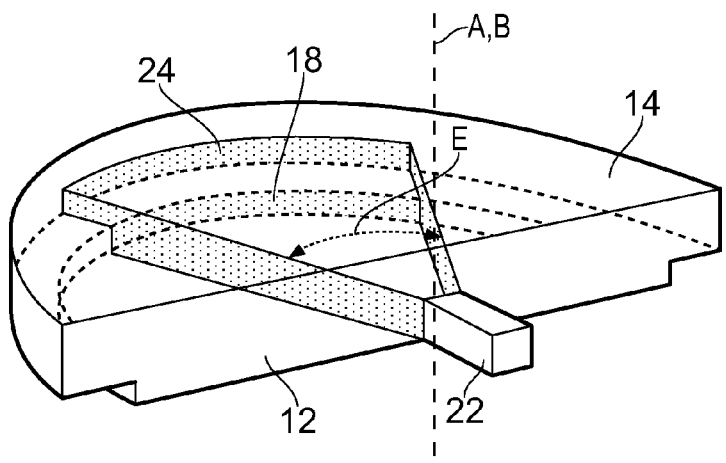
FIG. 2 is a perspective view of the calibration block of FIG. 1, showing a transducer coupled to the input region thereof.

FIGS. 1 and 2 show a calibration block 10 according to an embodiment of the present invention. The calibration block 10 is suitable for calibrating the signal sensitivity of an angular scanning phased array ultrasonic testing scanner (not shown) having a signal sensitivity calibration program, such as the Omniscan MX scanner marketed by Olympus. Functionality is also provided for setting the calibration gain. Such calibration programs are well known in the art and as such for brevity will not be described in any detail. For more information, reference may be made to MXU SOFTWARE MANUAL 4.3.3.1 (SENSITIVITY CALIBRATION USING SIDE DRILLED HOLE)/SOFTWARE MANUAL 4.3.3.2 (SENSITIVITY CALIBRATION USING RADIUS/OLYMPUS PHASED ARRAY INSTRUMENTATIN MANUAL CH 4.2 page 59/OMNISCAN CALIBRATION TECHNIQUES A.2.3 STEP 3 page 421).

The calibration block 10 is formed of an acoustically transmissive, material, which may be chosen to match the material to be tested. For example, in some embodiments the calibration block 10 may be formed from aluminium.

The calibration block 10 is generally semicircular in shape and has a generally planar front surface 12 which extends between a generally planar upper surface 14 and a generally planar lower surface 16. The upper and lower surfaces 14, 16 are both generally semicircular in shape. The upper surface 14 is larger than the lower surface 16 so as to define a step which extends in a curved manner around the calibration block 10. The curved step or shoulder defines an acoustically reflective surface or "calibration surface" 18 which is generally equidistant from a central axis A. The calibration surface 18 may therefore be considered to form part of a cylindrical wall. In the illustrated embodiment the radial distance R1 from the central axis A to the calibration surface 18 is 110 mm, but may have any suitable distance. The peripheral edge of the calibration block 10 forms a boundary surface 24. The radial distance R2 from central axis A to the boundary surface 24 is 125 mm, but may have any suitable distance. The calibration block 10 has a thickness T of 20 mm, but may have any suitable thickness. It is preferred that the calibration block has a thickness which is greater than or equal to the corresponding dimension of a transducer arranged to be used with it, an preferably at least twice the corresponding dimension. A block which is shorter than the transducer may cause erroneous signal response due to beam spread reflections.

The calibration surface 18 has a height S of 4 mm, but may have any suitable height; for example, the height of the calibration surface may be less than: 20 mm, 15 mm, 10 mm, 5 mm or 1 mm. Less than 5 mm is advantageous in applications such as testing aircraft components as this is often representative of a target feature (this is explained in more detail below). It is preferred that the height of the calibration surface 18 is between 0.5 mm and 5 mm.

The front surface 12 has a generally flat input region 12a which is arranged to be coupled to an ultrasound transducer 22 of the angular scanning ultrasonic testing scanner such that the transducer 22 may emit ultrasound into the calibration block 10 throughout a scanning envelope E. The beam of ultrasound generated by the transducer 22 moves angularly about a general beam axis B. The input region 12a is arranged to position the transducer 22 such that the path length of the primary wave front from the transducer 22 to the calibration surface 18 is generally equal for each beam angle across the scanning envelope E. This will be referred to herein as the "calibration configuration" of the transducer 22. In practice, "generally equal" will mean a travel path variance of less than or equal to 5%.

In the illustrated embodiment the input region 12a is arranged to be directly coupled to the transducer such that the emission face of the transducer 22 is flush with the flat input region 12a and the central axis of the transducer is aligned with a centre line P of the block 10. In other embodiments the input region 12a may be arranged to be coupled to a transducer 22 via a wedge or shoe. The beam axis B may in some embodiments be generally coaxial with respect to the central axis A of the calibration surface 18. In some embodiments the input surface 12a may be shaped to conform to the coupling surface of the transducer 22, wedge or shoe; for example, the input surface 12a may have an arcuate profile.

In some embodiments the size of the acoustically reflective dimensions of the calibration surface 18 may be chosen to representative of the detectable defect size being sought; for example, the height of the calibration surface may be the same or similar in size to a target feature. This advantageously enables a calibration block according to embodiments of the present invention to be used both for sensitivity calibration and for gain calibration.

In the illustrated embodiment the calibration surface 18 extends through 180° about the central axis A. This advantageously enables sensitivity calibration across a wide scanning envelope of up to +90°>−90°. In other embodiments the calibration surface 18 may extend at least 40°, 60°, 90°, 120°, or 160°.

In use, with the transducer 22 in the calibration configuration, the sensitivity calibration feature of the angular scanning ultrasonic testing scanner can be operated to calibrate the signal sensitivity of the scanner using the signal response from the calibration surface 18. Following this, a user of the scanner may calibrate the signal gain using the signal response from the calibration surface 18 and in some cases thereafter perform a reference calibration to increase familiarity with the signal shapes and response from a target feature.

Figure 3:
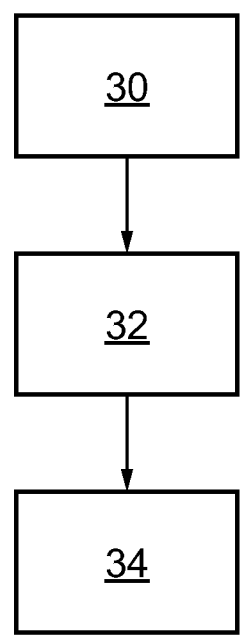
FIG. 3 is a flow chart showing a method according to an embodiment of the present invention.

FIG. 3 shows a method according to an embodiment of the present invention for calibrating the signal sensitivity of an angular scanning phased array ultrasonic testing scanner.

At step 30 a calibration block 10 according an embodiment of the present invention is provided.

At step 32 an ultrasound transducer of the ultrasonic testing scanner is coupled to the input region 12a of the calibration block 10 in the calibration configuration. A suitable couplant, such as a thixotropic gel, may be provided between the transducer 22 and input region 12a to improve the acoustic coupling between them.

At step 34 the sensitivity calibration feature of the ultrasonic testing scanner is operated such that the transducer 22 emits ultrasound into the calibration block 10 across a scanning envelope E and the signal response from the calibration surface 18 can be measured to calibrate the signal sensitivity of the ultrasonic testing scanner. In embodiments of the invention the envelope E may be any combination of negative and/or positive angles which lie within the physical boundary of the block. In some embodiments the ultrasonic testing scanner may be operated in a lateral scanning mode. The signal response from the calibration surface 18 can also be used to set the calibration gain of the scanner.

Figure 4:
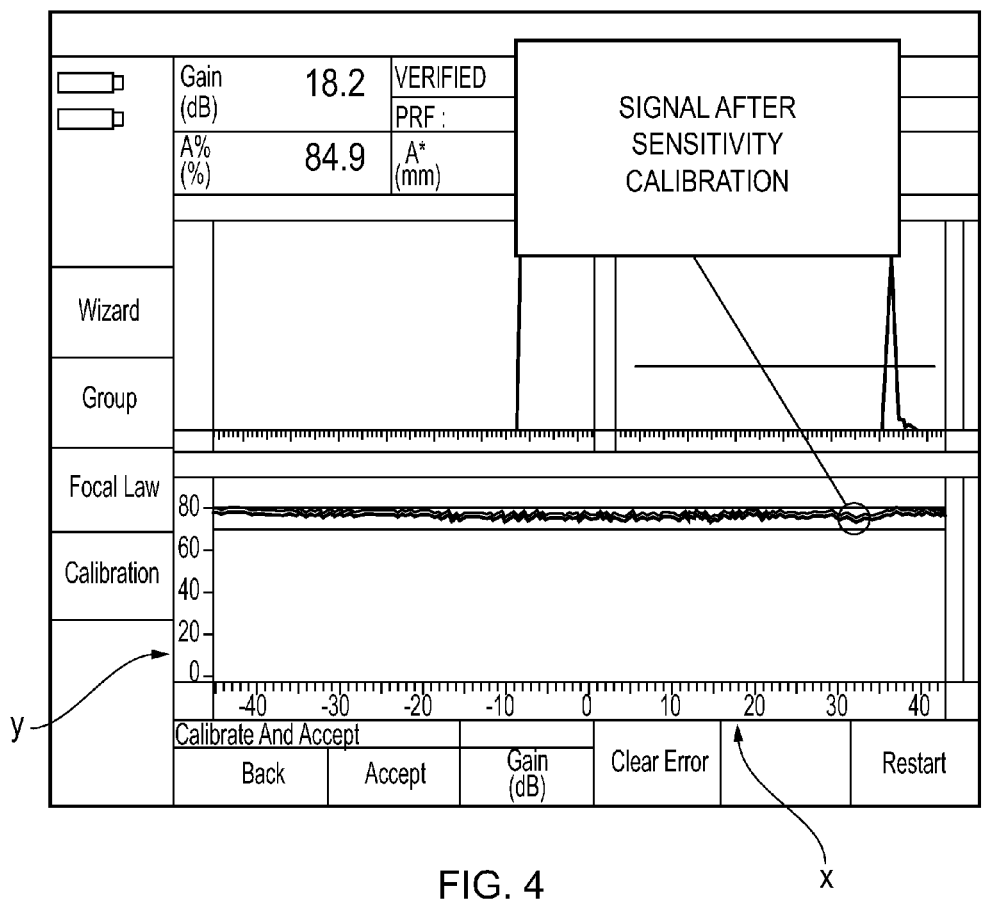
FIG. 4 is a plot showing the signal response from the calibration block of FIG. 1 after sensitivity calibration.

FIG. 4 shows a plot of the signal response from the calibration surface 18 once sensitivity calibration has been completed. The y axis represents the signal response and the x axis represents the beam angle and shows at least some of the scanning envelope E. As can be seen, the response variance across the scanning envelope E is now improved, in so much as a defect of an equivalent size detected at +/−45° now has a signal response equal to one at say +/−5°, which is an improvement on known sensitivity calibration for lateral scanning phased array ultrasonic testing scanners which in some cases are only effective over a narrower angular area.

The calibration block according to embodiments of the present invention may be configured in various sizes and forms in order to satisfy operation needs.

It has been found that a sensitivity calibration block according to embodiments of the present invention enables an easier and quicker method of sensitivity calibration over a wider range of angles than those supported by blocks suggested by the prior art. In particular it enables sensitivity calibration when using wider angle lateral scan, for example +/−45°. Moreover, a calibration block according to embodiments of the present invention can be used both for sensitivity calibration and for gain calibration.

Although the invention has been described above with reference to one or more preferred embodiments, it will be appreciated that various changes or modifications may be made without departing from the scope of the invention as defined in the appended claims.

The invention claimed is:

1. Use of a calibration block for calibrating the signal sensitivity and/or gain of an angular scanning phased array ultrasonic testing scanner arranged to generate a primary wave front at a plurality of contiguous beam angles across a scanning envelope, the calibration block being formed of an acoustically transmissive material and comprising: first major surface having a peripheral edge; a second major surface; a calibration surface disposed between general planes of the first and second major surfaces and configured to extend in a generally circular arc so as to be generally equidistant from a central axis, the peripheral edge of the first surface being spaced further from the central axis than the calibration surface; and an input surface for acoustically coupling to an ultrasound transducer of the ultrasonic testing scanner and being arranged to position the transducer such that the path length of the primary wave front from the transducer to the calibration surface is generally equal for each beam angle across the scanning envelope.

2. A method for calibrating the signal sensitivity of an angular scanning phased array ultrasonic testing scanner arranged to generate a primary wave front at a plurality of contiguous beam angles across a scanning envelope, the method comprising:
   providing a calibration block formed of an acoustically transmissive material and comprising: first major surface having a peripheral edge; a second major surface; a calibration surface disposed between general planes of the first and second major surfaces and configured to extend in a generally circular arc so as to be generally equidistant from a central axis, the peripheral edge of the first surface being spaced further from the central axis than the calibration surface; and an input surface;
   coupling an ultrasound transducer of the ultrasonic testing scanner to the input surface of the calibration block, the calibration surface is positioned with respect to the transducer such that the path length of the primary wave front from the transducer to the calibration surface is generally equal for each beam angle across the scanning envelope; and
   calibrating the signal sensitivity of the ultrasonic testing scanner by measuring the signal response from the calibration surface.

3. A method according to claim 2, wherein the input surface is generally parallel with respect to the central axis of the calibration surface.

4. A method according to claim 2, wherein the input surface is parallel with respect to a tangential plane to the calibration surface.

5. A method according to claim 2, wherein the size of the calibration surface is selected to be representative of a defect the scanner is arranged to detect.

6. A method according to claim 2, wherein the height of the calibration surface is less than or equal to 5 mm.

7. A method according to claim 2, wherein the calibration surface extends through an arc of at least 90°.

8. A method according to claim 7, wherein the calibration surface extends through an arc of generally 180°.

9. A method according to claim 2, wherein the peripheral edge of the first surface is spaced further from the central axis than the calibration surface by at least ¼ of the distance between the central axis and the calibration surface.

10. A method according to claim 2, including the step of calibrating the signal gain of the ultrasonic testing scanner by measuring the signal response from the calibration surface.

11. A method according to claim 2, whereby the scanning envelope is at least 90°.

12. A method according to claim 2, whereby the scanning envelope is a lateral scanning envelope.

* * * * *